United States Patent [19]

Sweeney et al.

[11] Patent Number: 5,665,555
[45] Date of Patent: Sep. 9, 1997

[54] **METHOD OF DETERMINING THE EFFECT OF A TEST SUBSTANCE ON A CLONE OF A *CENTROPTILUM TRIANGULIFER* MAYFLY**

[75] Inventors: Bernard W. Sweeney, West Grove; David H. Funk, Lincoln University, both of Pa.; Laurel June Standley, Wilmington, Del.

[73] Assignee: Academy of Natural Sciences of Philadelphia, Philadelphia, Pa.

[21] Appl. No.: 168,099

[22] Filed: Dec. 15, 1993

[51] Int. Cl.[6] .................................................. C12Q 1/02
[52] U.S. Cl. .......................... 435/7.21; 424/9.2; 435/4; 435/29; 436/63; 436/126; 436/153; 436/164; 436/171; 436/173; 436/177
[58] Field of Search .......................... 435/4, 7.21, 7.92, 435/29; 436/63, 126, 153, 164, 171, 173, 177; 424/9, 9.2

[56] References Cited

U.S. PATENT DOCUMENTS

| | | | |
|---|---|---|---|
| 4,701,406 | 10/1987 | Chou | 435/7 |
| 4,748,127 | 5/1988 | Siepmann et al. | 436/50 |
| 4,808,517 | 2/1989 | Blondin et al. | 435/4 |
| 5,094,944 | 3/1992 | Hayes | 435/29 |
| 5,149,656 | 9/1992 | Bitton et al. | 435/288 |
| 5,175,091 | 12/1992 | Hannan | 435/29 |
| 5,198,336 | 3/1993 | Knobeloch et al. | 435/4 |
| 5,225,333 | 7/1993 | Krause | 435/32 |

OTHER PUBLICATIONS

"Standard Methods for the Examination of Water and Wastewater," prepared and published jointly by: American Public Health Assoc., American Water Works Assoc. & Water Environment Federation, 18th Edition, pp. 8–78 to 8–82 & Cover Sheet (1992).

Bernard W. Sweeney et al., "Influence of Food Quality and Temperature on Life History Characteristics of the Parthenogenetic Mayfly, *Cloeon triangulifer*," *Freshwater Biology* 14, pp. 621–630 (1984).

John E. Brittain, "Biology of Mayflies," *Ann. Rev. Entomol.*, 27, pp. 119–147 (1982).

Paul E. Woods et al., "Genetic Variation in Laboratory and Field Populations of the Midge, *Chironomus tentans* Fab.: Implications for Toxicology," *Environmental Toxicology and Chemistry*, 8, pp. 1067–1074 (1989).

"Standard Methods for the Examination of Water and Wastewater," prepared and published jointly by: American Public Health Assoc., American Water Works Assoc. & Water Pollution Control Federation, 17th Edition, pp. 8–81 to 8–84 & Cover Sheet (1989).

Richard Y. Lamb et al., "Cytological Mechanisms of Thelytokous Parthenogenesis in Insects," Department of Biological Sciences, University of Illinois, pp. 367–369 (1987).

Esko Suomalainen et al., "Cytology and Evolution in Parthenogenesis," CRC Press, Inc., Boca Raton, Florida, pp. 4–5, 22–39 and 112–117 (1987).

L.M. Tabak et al, *Hydrobiologia*, 218, 157–166, 1991.

*Primary Examiner*—David Saunders
*Attorney, Agent, or Firm*—Panitch Schwarze Jacobs & Nadel, P.C.

[57] ABSTRACT

A method of determining the effect of a test substance on any life stage of at least one clone of a *Centroptilum triangulifer* mayfly comprising (A) identifying and selecting at least one clone of *Centroptilum triangulifer* as a test clone to be subjected to the test substance; (B) exposing each test clone to the test substance for a predetermined time; and (C) determining the effect of the test substance on each test clone by at least one of (i) observing the test clone for a lethal or sublethal effect and (ii) Sacrificing the test clone, and analyzing the sacrificed test clone for at least one of (a) the presence of at least one of the test substance and any of its metabolites, (b) the quantity of at least one of the test substance and any of its metabolites, and (c) a lethal or sublethal effect of at least one of the test substance and any of its metabolites. In a preferred embodiment for testing for a substance and any of its metabolites, the substance and any metabolites being tested are extracted and separated from the sacrificed mayflies in a solvent mixture, and the substance and any metabolites are identified and quantified using appropriate equipment and techniques.

16 Claims, 4 Drawing Sheets

METHOD OF DETERMINING THE EFFECT OF A TEST SUBSTANCE ON A CLONE OF A *CENTROPTILUM TRIANGULIFER* MAYFLY

FIELD OF THE INVENTION

This invention relates to bioassay techniques utilizing a unique bioassay organism, and in particular, the aquatic insect *Centroptilum triangulifer* (McDunnough), a species that was recently transferred from the genus Cloeon (McCafferty and Waltz, *Transactions of the American Entomological Society*, 116:769–799, 1990).

BACKGROUND OF THE INVENTION

The development of industry and the encroachment of civilization upon established ecosystems often places the interests of commerce at odds with the need to maintain a delicate balance in the ecosystem involved. Consequently, it has become increasingly important to establish the presence, persistence, biological availability, and biological effect of chemical contaminants introduced or about to be introduced into ecosystems using biological monitoring and toxicity testing procedures.

Insects have played a prominent role in toxicity testing and biological field monitoring for environmental contaminants. Standard methods have been established for raising and experimenting with a wide variety of terrestrial species in laboratories, whereas toxicity testing in water, especially freshwater stream and river ecosystems, has relied primarily upon fish and a few noninsect invertebrates, mainly Crustacea (e.g., *Daphnia magna, D. pulex*, Ceriodaphnia sp., Artemia sp., *Hyalella azteca, Grammarus lacustris* and the like). Unfortunately, many test species being used are not representative of the most species rich, abundant and productive group of organisms inhabiting streams and rivers, namely, aquatic insects. Aquatic insects are also potentially the group of organisms most vulnerable to the intrusion of toxins into the ecosystem.

Only a few species of aquatic insects such as the nonbiting midges *Chironomus tentans* and *C. riparius* and the burrowing mayflies *Hexagenia rigida* and *H. limbata* have been used routinely in bioassay studies, both chronic and acute. However, such species are less than ideal. For example, Hexagenia is difficult to culture and usually reproduces only once a year at most, making whole-life bioassays practically impossible. Species such as *C. tentans* has a shorter developmental period but are nevertheless difficult to work with because of the problems involved in mating adults, initiating experiments with genetically unknown and non-uniform size larvae, handling small eggs, and so on. Both Hexagenia and Chironomus tend to be sediment dwellers, inhabiting large lakes and rivers (Hexagenia) or predominantly lentic (Chironomus) rather than lotic habitats. Thus, they are well suited for sediment bioassays but not for other types of assays.

Although insects are the principal consumer organisms in most stream and river ecosystems worldwide, there is a paucity of stream insect species available as standard test organisms for laboratory and field bioassay procedures. This deficiency arises because it is difficult to establish laboratory colonies when, typically, stream and river insect larvae must be reared in a flowing water system in order to satisfy respiration and/or feeding requirements. Further, stream and river insects generally have long life cycles (e.g., 6–12 months) and the adults often have unusual behavioral requirements for reproduction such as elaborate mating swarms or flights, which make the establishment of laboratory colonies unfeasible.

Accordingly, it is important to provide a new bioassay organism which typifies higher animals in toxicity testing and biological field monitoring while representing the most vulnerable as well as the principal consumer organisms in most stream and river ecosystems. Further, the new bioassay organism must have a short life cycle and strictly controllable reproduction requirements while being amenable to analysis using any suitable procedure. The stream mayfly, (Insecta: Ephemeroptera) *Centroptilum triangulifer* McDunnough (hereinafter *C. triangulifer*), satisfies these criteria and overcomes the problems mentioned above relating to the use of other aquatic organisms as bioassay organisms.

SUMMARY OF THE INVENTION

The invention provides a method of testing for the presence of any substance in an environment to which any life stage of a *Centroptilum triangulifer* mayfly is exposed and which has an effect on the mayfly comprising collecting a sample of *Centroptilum triangulifer* mayflies exposed to the substance to be tested, and determining the effect of the substance on the mayfly by at least one of (a) observing the mayfly for a lethal or sublethal effect and (b) sacrificing individual mayflies, and analyzing the sacrificed mayflies for at least one of (i) the presence of at least one of the substance and any of its metabolites, (ii) the quantity of at least one of the substance and any of its metabolites and (iii) a lethal or sublethal effect of at least one of the substance and any of its metabolites.

In a preferred embodiment for testing for a substance and any of its metabolites, the substance and any metabolites being tested are extracted and separated from the sacrificed mayflies in a solvent mixture, and the substance and any metabolites are identified and quantified using appropriate equipment and techniques.

DETAILED DESCRIPTION OF THE PREFERRED EMBODIMENTS

The invention is illustrated in the accompanying drawings and described herein by reference to a preferred analytical procedure using chlordane as an illustrative substance to be identified and quantified. It is to be understood that the invention is neither limited to the preferred analytical technique nor to the detection of chlordane.

Indeed, the process of the invention can be employed to identify and quantify any substance in an environment to which *C. triangulifer* is exposed. The analysis preferably includes an analysis of the lethal and sublethal effects of any substance to which *C. triangulifer* is exposed, such as stressor substances, contaminants and suspected contaminants. Examples of such substances include toxicants which have a deleterious effect on living organisms such as, for example, copper, cadmium, mercury, zinc, chromium, phenol, benzene, formaldehyde, toluene, other organics such as chlorinated organics including pesticides and contaminants such as lindane, toxaphene, polychlorinated biphenyls (PCBs), polychlorinated dibenzo-p-dioxins or dibenzofurans (PCDD/PCDF), polychlorinated benzene, polychlorinated phenols, dichlorodiphenyltrichloroethane (DDT) and the like. Various other classes of pesticides including insecticides, herbicides and acaracides such as triazines including atrazine and cyanazine, organophosphates such as chlorpyrifos, carbamates such as carbofuran, organochlorines such as endosulfan, and other organic chemical compounds used for a variety of domestic and industrial purposes including detergents, degreasers and the like and mixtures thereof can be tested for toxicity and lethal and sublethal effects.

All inorganic chemicals including nutrients, metals, pH, alkalinity, hardness, microbial pesticides such as *Bacillus thuringiensis israeliensis*; effluents from industrial plants and commercial facilities such as paper mills, chemical manufacturing, paint production, automobile manufacturing and the like; effluents from sewage treatment plants, landfills, and the like; mining waste effluent or runoff such as in petroleum or metals extraction, non-point runoff such as agricultural runoff including pesticides, fertilizers, nutrients, trace metals; roadway runoff including petroleum hydrocarbons, trace metals, polycyclic aromatic hydrocarbons, other combustion products, and the like; urban and suburban runoff; chemical warfare agents; medical products including effluent from sewage or production facilities; spillage; chemicals produced which may reach the fresh water environment during use, transport, or following disposal; various salts including sulfides, and any other substance that *C. triangulifer* could be exposed to and consequently be assayed using the unique bioassay organism of the invention and any suitable analytical technique.

Chlordane was chosen as illustrative, since it continues to be used throughout much of the world for pest control although its use in the United States was banned by the Environmental Protection Agency (EPA) in 1988. Chlordane is nonpolar, persistent, and likely to bioaccumulate. It has been measured in the tissues of organisms worldwide and has recently been added to the EPA's RCRA list of regulated toxic compounds in waste and wastewater.

Any suitable analytical technique can be employed with the unique bioassay organism of the invention including ELISA (enzyme linked immunosorbent assay), LISA (liposomal immunosorbent assay), gel electrophoresis, gas chromatographic separation and identification using detectors such as a mass spectrometer, flame ionization detector, electron capture detector, nickel/phosphorous detector, infrared detector and the like. Liquid chromatographic separation and identification using detectors such as ultraviolet or visible detectors, fluorescence and the like, as well as atomic absorption (AA), ion charge plasma (ICP), direct charge plasma, ultraviolet/visible spectrophotometry or any other suitable method known in the art can be employed. In fact, any and all methods used to detect any chemical target compound or its breakdown products can be employed as well as biological isolation methods for bacterial agents, and the like.

Tests for the presence, amount and lethal and sublethal effects from any source are also contemplated, including any source from which the substance may reach a fresh water environment during use, transport or after disposal, such as effluent, runoff and spillage, as well as from sedimentation from non-point sources such as agriculture or urban development, or point sources such as outflows.

In addition to having at least potentially lethal effects on *C. triangulifer*, a substance may have sublethal effects on *C. triangulifer* which make it valuable as a bioassay organism. Sublethal effects include, for example, size, mass, fecundity, behavior, molting, growth, respiration, feeding, digestion, assimilation, egestion, excretion, morphology, mobility, susceptibility to parasite attack, effect on developmental stages, chemosensory ability, effect on tactile sensing ability, endocrine levels, enzymatic induction or combinations thereof. Many of the sublethal effects may be determined by careful observation without the need to sacrifice the mayflies being tested.

*C. triangulifer* has several characteristics that make it well suited as a bioassay organism. It has a relatively short life cycle for an aquatic insect (about 43 days from egg to adult at 25° C.) which makes possible the completion of several life cycle experiments within the period of a year. Female adults are parthenogenetic, lack elaborate reproductive behavior and readily oviposit under laboratory conditions in small 30 ml jars. *C. triangulifer* egg and larval stages can be readily reared to eclosion or metamorphosis, respectively, under a variety of laboratory conditions (temperature, food quality, photoperiod, and so on) in small, static vessels and do not require flowing water, even though they naturally inhabit lotic systems. Important lift history characteristics of *C. triangulifer* such as egg development, larval growth, subimago development, adult (imago) size, fecundity, and so on can be readily quantified under controlled laboratory conditions.

*C. triangulifer* mayflies are very sensitive to environmental perturbation. It is an important species of aquatic insect (Ephemeroptera) which inhabits small to intermediate sized streams in northeastern North America. Aquatic insects are an important component of the fauna of most natural streams and rivers worldwide.

The extent and nature of genetic variability in laboratory populations of standard bioassay animals such as Chironomus and Daphnia have been shown to be significant factors underlying the lack of repeatability of standard bioassay results between laboratories. Accordingly, regular genetic monitoring is becoming a standard protocol for laboratories using bioassay techniques and biological organisms. While the monitoring of the genetic structure of bioassay populations is a step in the right direction, it does not resolve the problem. By contrast, bioassays carried out using specific clones of *C. triangulifer*, which requires genetic characterization of only a few randomly selected individuals, provide quality assurance and quality control for the genetic component of entire assays using only one clone.

Three primary reasons that *D. magna* has been widely preferred as a bioassay organism are its ease of laboratory culture, its high sensitivity, and its clonal method of reproduction. *C. triangulifer* shares all three advantages, including clonal reproduction. The clonal nature of parthenogenesis in *C. triangulifer*, by which offspring from the female are genetically identical to the female in the absence of mutations, since there is no mating with males involved, makes possible the elimination of genetic variability in all life stages and the problems derived therefrom. This makes it possible to eliminate the possibility that one or more genotypes having different propensities to bioaccumulate a pollutant is a causative factor in observed variations in average body burden of a pollutant or its metabolites. As a result, *C. triangulifer* is especially attractive for elucidating the physiological mechanism of a toxicant where genetic variation might otherwise obscure the mechanism under study.

Figure 1:
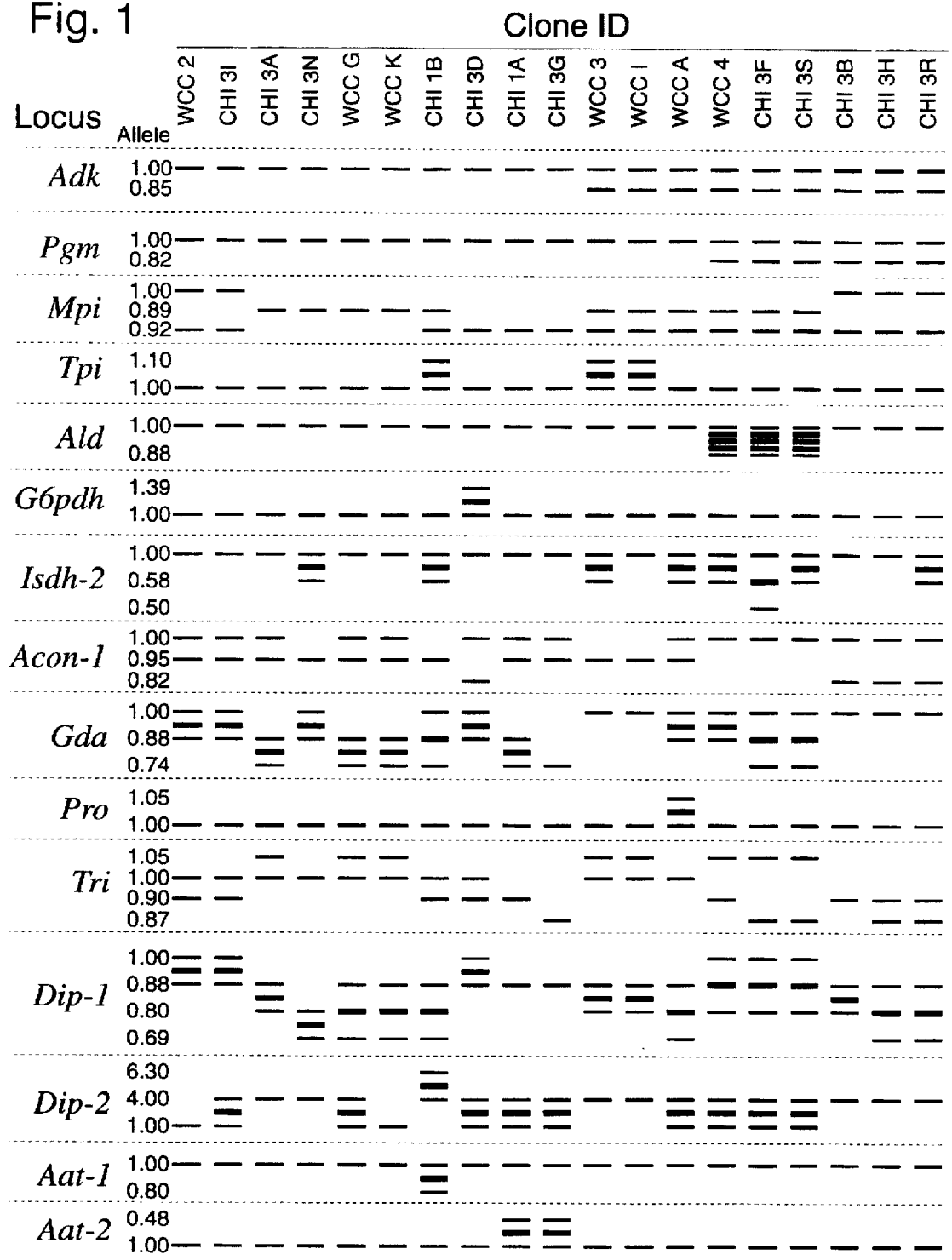
FIG. 1 shows the electrophoretic banding pattern for each of the nineteen clones of *C. triangulifer* that have been characterized to date. In this figure, each locus represents a different enzyme used to characterize each clone.

Nineteen distinct genetic clones (genotypes) of *C. triangulifer* have been isolated from wild populations, indicating substantial genetic heterogeneity within the species (See FIG. 1). In the figure, each column shows the distinctive electrophoretic banding pattern for each of the nineteen clones presently known to exist for *C. triangulifer*. Each row, or locus (e.g., Adk, Pgm, etc.) represents a distinct protein (in this case all are enzymes) which is coded for by DNA at a specific location (locus) on the chromosomes of the mayfly. For a normal sexually reproducing diploid organism, each locus will be represented on two (homologous) chromosomes (one from the mother and one from the father). In parthenogenetic mayflies such as *C. triangulifer*, both chromosomes are inherited from the mother. Each enzyme is therefore coded for at two locations.

The enzymes coded for at these two locations may be identical, in which case the individual is considered homozygous, or they may be different, in which case the individual is considered heterozygous. Differences usually result in minor changes in electric charge of the enzyme products, and consequently, changes in the mobility of the enzyme in an electric field. Enzymes produced by homozygous individuals will have a single mobility and will therefore show up as a single band when the gel is stained for that enzyme. Heterozygous individuals produce two forms of the enzyme with differing mobilities, resulting in two or more bands on the gel (depending on the subunit structure of that enzyme).

Within a locus, different forms of an enzyme are referred to as alleles which are identified by numbers (e.g., 1.00, 0.85, etc.) indicating their electrophoretic mobility relative to the allele found in clone WCC 2 (always represented by 1.00). For example, clone WCC 2 is homozygous for allele 1.00 at locus Adk, whereas clone WCC 3 has two forms of Adk (i.e., is heterozygous), resulting in two bands, 1.00 and 0.85. Each clone has a distinctive combination of banding patterns across the 15 loci we use to identify them. For example, the clones WCC 2 and CHI 31 are identical at all loci except Dip-2, where WCC 2 is homozygous for allele 1.00 and CHI 3I is heterozygous for alleles 1.00 and 4.00. Since all the offspring from a *C. triangulifer* mother are genetically identical to the mother (in the absence of mutations), they will exhibit the same banding patterns and will therefore be identifiable as such.

The ability to choose among the nineteen clones of *C. triangulifer* makes it possible to address the role of genetic variation in susceptibility to a toxic substance, if desired, by including more than one clone in the experimental design. The problem of interactive effects between genotype and environment could thus be explored. For example, it would be valuable to know if the sensitivity of different clones reared under the same exposure to toxins differed significantly and whether there was a consistent rank order in their response to the toxins. Thus, by choosing the appropriate clone or clones of *C. triangulifer*, one can specifically control the genetic variability involved in the bioassays.

In order to be useful, toxicity studies involving freshwater aquatic insects must be logistically straight-forward and repeatable. The use of a range of species in bioassay testing is very helpful to the adequate evaluation and/or prediction of the impact of a chemical on a particular environment. *C. triangulifer* is sensitive to low concentrations of pollutants and fits the recommended criteria for toxicity studies better than the cultured organisms used heretofore, the variety and variability of which cannot be controlled. For example, it is clear from LC50 survivorship data shown in the examples (LC50 is the concentration of toxin which produces 50% lethality in test organisms) that the amount of technical chlordane to which *C. triangulifer* can be exposed cannot exceed 4.3 µg/l. This indicates that *C. triangulifer* larvae are substantially more sensitive to technical chlordane than other aquatic macroinvertebrates that have been tested to date including Chironomus and *G. lacustris* which have LC50 values of 15 and 26 µg/l, respectively.

The parthenogenetic mode of reproduction for *C. triangulifer*, combined with a relatively short embryonic and larval developmental period and overall ease of maintaining laborator cultures provides a useful and effective bioassay system for evaluating toxins of all kinds.

While *C. triangulifer* is described herein in detail by reference to its use in detecting chlordane levels using specific testing procedures, it is to be understood that *C. triangulifer* can also be employed to detect other chemicals and pollutants, as well as other substances, using any other suitable bioassay or testing technique.

The invention is further illustrated but is not intended to be limited by the following examples in which all parts and percentages are by weight unless otherwise indicated.

All examples herein were carried out using the WCC 2 clone isolated from White Clay Creek. The test procedures and data obtained as a result of the WCC 2 clone are similar to those procedures used to test and the type of data which can be expected from using any of the other clones.

EXAMPLE 1

Assessment of the Genetic Structure of *C. triangulifer* Using Allozyme Electrophoresis The utility and effectiveness of *C. triangulifer* for whole life bioassay was confirmed using allozyme electrophoresis to confirm its genetic structure. Adults were stored individually at −80° C. until examined electro-phoretically. Allozymes, which are different forms of the same enzyme, were separated by horizontal starch gel electrophoresis. Briefly, gels consisted of about 11% potato starch (Starch Art Corporation) in 250 ml of gel buffer and measured 18.5× 14.6×0.6 cm thick. Each adult was ground in a porcelain depression plate containing at least 20 µl deionized water. Soluble proteins were absorbed onto six paper wicks (2×7 mm; Whatman, Clifton, N.J., No. 3 filter paper). One wick was applied to each of six gels at a slice made 5.5 cm from the cathode end of the gel. Gels were cooled during the experiment by placing aluminum trays containing ice on the gel surface, which was covered with Reynolds 910 film for electrical insulation. After electrophoresis, each gel was sliced into four horizontal slabs, each of which was stained separately for one or more enzymes. At least 25 enzymes, representing a total of 30 loci, were assayed for each specimen. Staining solutions for most enzymes were applied as 2% agar overlays, except for aspartate aminotransferase, for which the gel was immersed in stain.

Thirty adults of *C. triangulifer*, twenty five from the test clone and five from a control clone, which served as a reference for all experiments, were examined electrophoretically on each gel. Bands of a particular mobility were interpreted as alleles, and frequencies were calculated for each allele. All presumed allelic homologies were verified in subsequent tests by comparing a few representatives from each clone on the same gel.

Genetic variation within two natural populations of *C. triangulifer* in Pennsylvania was quantified (White Clay Creek [39° 51'N; 75° 47'W] and Chillisquaque Creek [41° 03'N; 76° 41'W]). Nineteen distinct genetic clones of *C. triangulifer* were isolated. This shows that levels of genetic variation exist among *C. triangulifer* clones that are comparable to levels observed among local populations of bisexual mayfly species. This enables the investigator to choose a priori the level of genetic variation to be included in the experimental design which can range from none (using only one clone) to about the level found in local populations of normal bisexual mayflies of other strains (as many as all nineteen clones can be used). This provides a real advantage in carrying out a bioassay.

Figure 2:
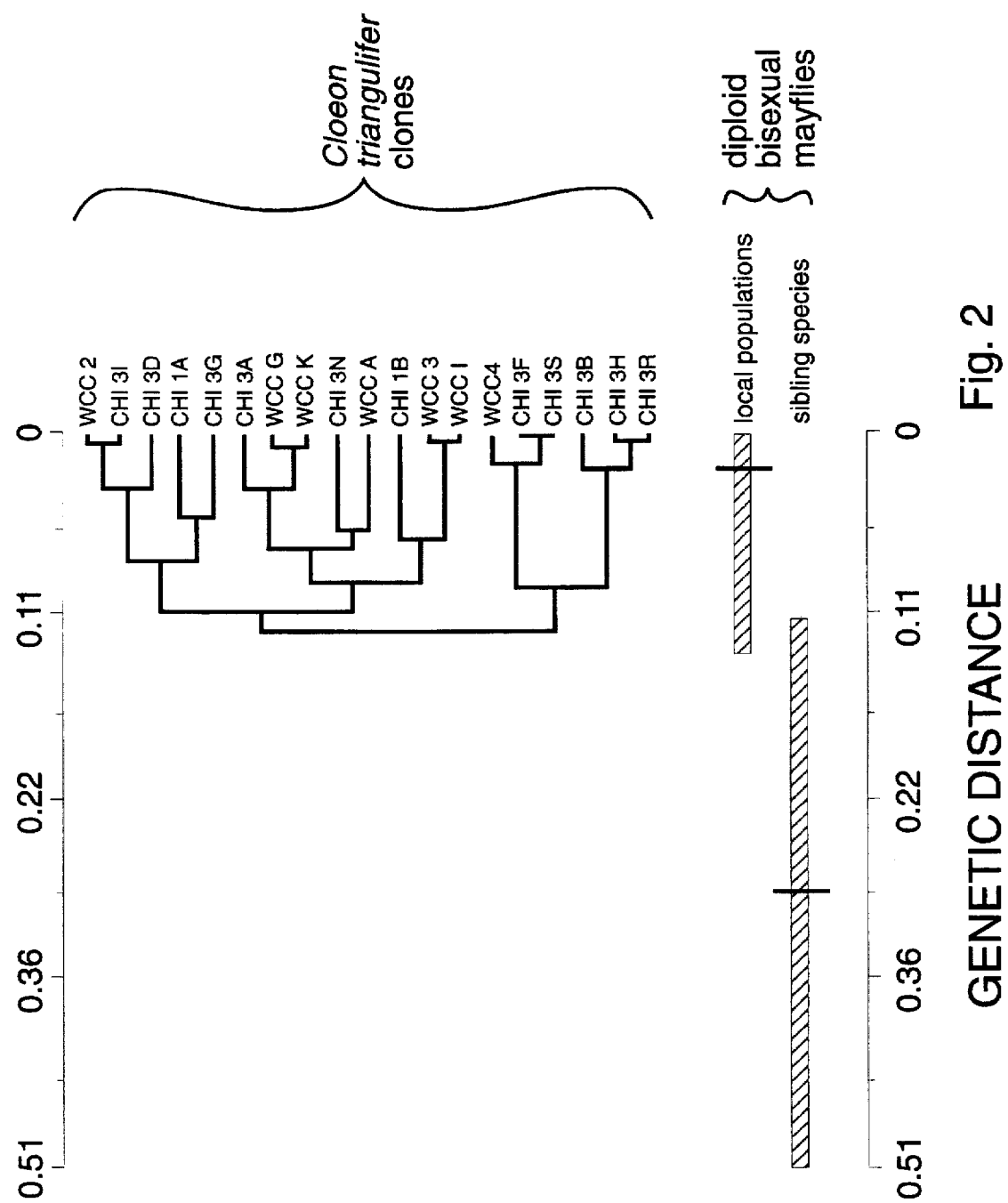
FIG. 2 is a phenogram using Nei's measure of the accumulated number of gene substitutions per locus (genetic distance) and showing the genetic distance between 19 clones of *C. triangulifer* that occur in White Clay Creek and Chillisquaque Creek, Pa. (Nei, M., Genetics 89:583–590, 1978).

The magnitude of genetic variation among the clones (as indicated by Nei's genetic distance) ranged from 0.004 to 0.183 (FIG. 2). The phenogram of FIG. 2 shows this genetic distance, which is a measure of the accumulated number of gene substitutions per locus, and the degree of genetic similarity among the nineteen clones of *C. triangulifer* occurring in White Clay Creek and Chillisquaque Creek, Pa. Distances were calculated from allele frequency data for 30 enzyme loci. For comparison, the average (represented by the vertical bar) and range (represented by the cross-hatched horizontal bar) of genetic distance between local, intraspecific populations located within 200 km of each other, as well as populations of sibling species, are shown for diploid bisexual mayflies, compared to the *C. triangulifer* parthenogenic mayflies of the present invention. The bracketed pairs or groups of *C. triangulifer* clones indicate the relative degree of distance between the pairs or groups in accordance with the horizontal distance of the brackets. Thus, for example, WCC 2 and CHI 3I are rather closely related to each other, but are relatively genetically distant from CHI 3R.

The clonal nature of parthenogenetic reproduction has been confirmed by the absence of allozyme differences between a given mother and her offspring, as well as in the field where individuals in natural populations cluster biochemically into distinct genotype classes or clones that have been found year after year.

EXAMPLE 2

Chlordane Preparation

Technical chlordane (catalog no. P-017N from Accustandard, Inc., New Haven, Conn.) is an insecticide consisting of a mixture of chlorinated methanoindenes dominated by compounds containing seven to nine chlorine atoms. For all experiments, technical chlordane was dissolved in methanol and added to enough filtered (0.45 µm) stream water to give the desired test concentrations. Two control treatments of stream water were used: one with 50 µl methanol and one without methanol (hereinafter referred to as the nonmethanol control). This allowed separate evaluation of direct chlordane effects from indirect effects of the solvent. Survivorship in the methanol control was the same as that in the nonmethanol control. Accordingly, methanol did not contribute significantly to toxicity in the experiments.

Egg Development and Hatch Success, Larval Survivorship, Growth, and Development Rate Eggs were placed in glass jars (6.5 cm deep; 5.5 cm diameter) containing 30 ml of test solution. All eggs in a given jar were deposited by a single female; 54 females of clone WCC 2 (an iso-female parthenogenetic line started from an adult female collected from White Clay Creek, Chester County, Pa., in 1989) were used to establish six replicates each of the two controls and seven treatment conditions (i.e., chlordane concentrations of 5.0, 8.9, 15.8, 28.1, 50.0, 89.0, and 158.3 µg/l). Each jar contained about 1,000 to 2,000 eggs. Chlordane was added immediately following oviposition, using micropipettes. Eggs were incubated at 20°±0.1° C. Eggs were examined daily for the onset of hatching. After hatching had ceased, each clutch was examined to determine hatch success.

For larvae, preliminary experiments performed at 0.005, 0.05, 0.5, 5.0, and 50 µg/l concentrations indicated that larval mortality occurred largely between concentrations of 5 and 50 µg/l. Six replicates for each of two control (methanol and nonmethanol) and five initial treatment concentrations (5.0, 8.9, 15.8, 28.1, and 50.0 µg/l) were used. For each replicate, chlordane was added at the beginning of the experiment. In three of the replicates for a given concentration, the water was changed and fresh chlordane was added halfway through the experiment (day 16). Water samples (100 ml) were taken from each jar at the start of the experiment, frozen, and later analyzed by GC electron-capture negative ionization mass spectrometry (ENCI-MS) to show the actual initial concentrations for the 5.0, 8.9, 15.8, 28.1, and 50.0 µg/l treatments to be 4.3, 9.4, 15.4, 27.4, and 56.3 µg/l, respectively.

Thirty newly hatched, first-instar larvae of *C. triangulifer* were placed in each of 42 experimental vessels (six replicates for each of seven treatments). Vessels were 1.9 l mason jars containing 1.5 l of unfiltered White Clay Creek water (total hardness, alkalinity, sulfate, and chloride levels in White Clay Creek water at the time of the experiment averaged 82.57, 59.3, 14.5, and 9.6 mg/l, respectively, with an average pH of 7.4; background levels of chlordane in White Clay Creeks were 0.00011 µg/l). Each vessel was submerged halfway in a 20°±0.1° C. circulating water bath. Light was provided by two Durotest Vita Light fluorescent lights with a timer providing a photoperiod of 13.5:10.5 h light:dark. An airstone kept dissolved oxygen levels at saturation. A small cylindrical plastic cage with a 1 mm Nitex™ netting top was placed over each jar to capture emerging adults.

Periphyton was grown on clear acrylic plates (70×200; 3 mm thick) in an artificial stream system enclosed by a greenhouse. One of these plates was placed in each vessel at the start of the experiment to provide a food source for the *C. triangulifer* larvae. Fresh plates were added twice during the experiment to ensure an adequate food supply.

Surviving *C. triangulifer* individuals from the various controls and treatment groups were collected daily as subimagos (pre-adults) from emergence cages. Most subimagos emerging from a given vessel were immediately killed, measured, dried, and weighed. The viability of eggs obtained from females that had been chronically exposed as larvae to the various control and treatment conditions was also assessed. Thus, a few subimagos from certain treatments were kept alive for 24 h (n=8, 5, 8, 6, 10, and 6 for the 4.3, 9.4, 15.4, 27.4, and 56.3 µg/l and control groups, respectively), during which time they molted to the adult stage and were allowed to oviposit into individual glass jars for assessing hatch success as described above. A few adults from the 4.3 µg/l group were frozen intact at 80° C. for later analysis for chlordane residue by electron capture negative ionization mass spectrometry (ECNI-MS). Chiordane residue in adults reared as larvae in 0.005, 0.05, and 0.5 µg/l treatments was also determined.

Eggs began hatching 9 d after oviposition in all 54 jars representing the two control and seven treatment conditions (5.0, 8.9, 15.8, 28.1, 50.0, 89.0, and 158.3 µg/l). Hatch success exceeded 95% for all replicates representing all treatments.

For larval experiments, a Dunnett's t test (Zar, J. H., *Biostatistical Analysis*, Prentice-Hall Inc., pp 157–159 (1974)), which compares a control mean to the means of each other group being tested, revealed no significant difference between the methanol and nonmethanol control groups, so only the methanol group was used for subsequent analyses of chlordane treatment effects. Also, analysis of variance (ANOVA) showed that for a given treatment level there was no significant difference for any of the parameters between the groups treated with chlordane only once (day 1) and those retreated on day 16. For-this reason, both groups were combined for all subsequent analyses.

Figure 3A:
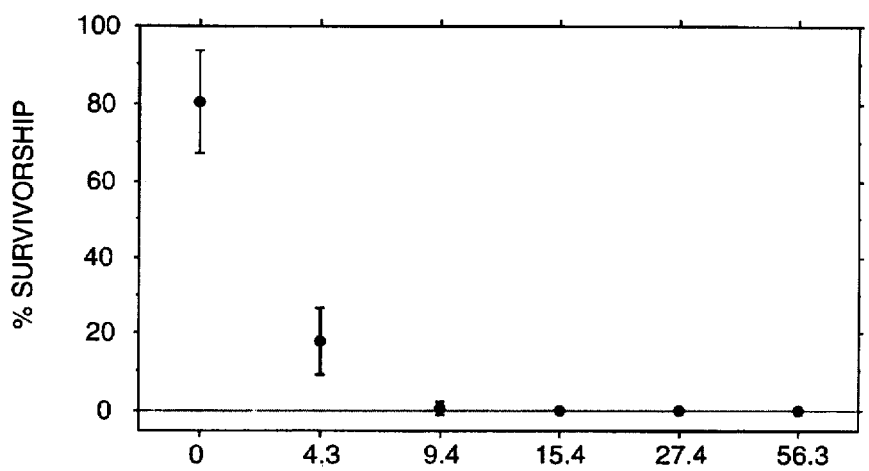
FIG. 3 shows (a) larval survivorship, (b) the duration of the larval growth period, and (c) adult female dry mass, as well as the fecundity (i.e., number of eggs per adult female) of the population for *C. triangulifer* after exposure to various levels of chlordane.

Larval survivorship averaged about 80% for both the methanol and the nonmethanol control groups, 18% for the 4.3 µg/l treatment, <0.6% for the 9.4 µg/l treatment, and zero for chlordane concentrations greater than or equal to 15.4 µg/l (FIG. 3a). These differences were statistically significant (ANOVA), with survivorship for the 4.3 µg/l treatment group (and higher) being significantly lower than the controls (Dunnett's t test; less than or equal to 0.05).

The average duration of the larval period or developmental time (FIG. 3b) and size of the adult at metamorphosis (FIG. 3c) were significantly longer (37 vs. 34.8 d) and larger (1.5 vs. 1.1 mg), respectively, for the 4.3 µg/l treatment group relative to the control groups (Dunnett's t test; $p \leq 0.05$). Statistical analysis of data for the 9.4 µg/l treatment group was not possible due to the low number of surviving individuals.

Figure 3B:
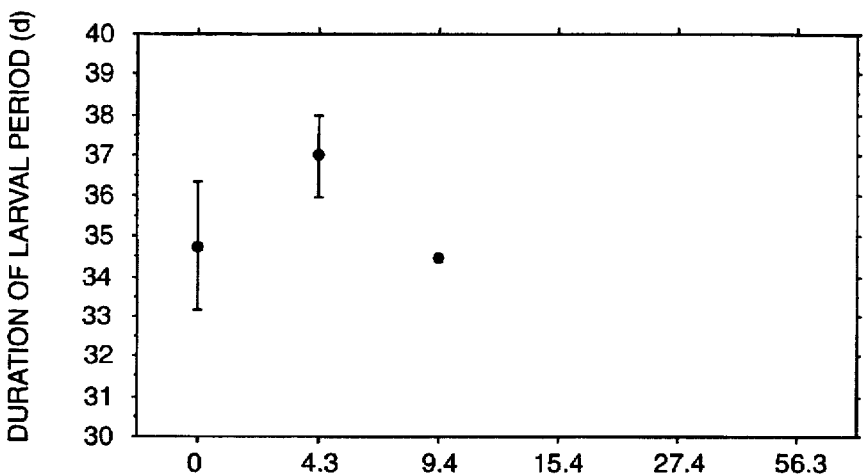
Figure 3C:
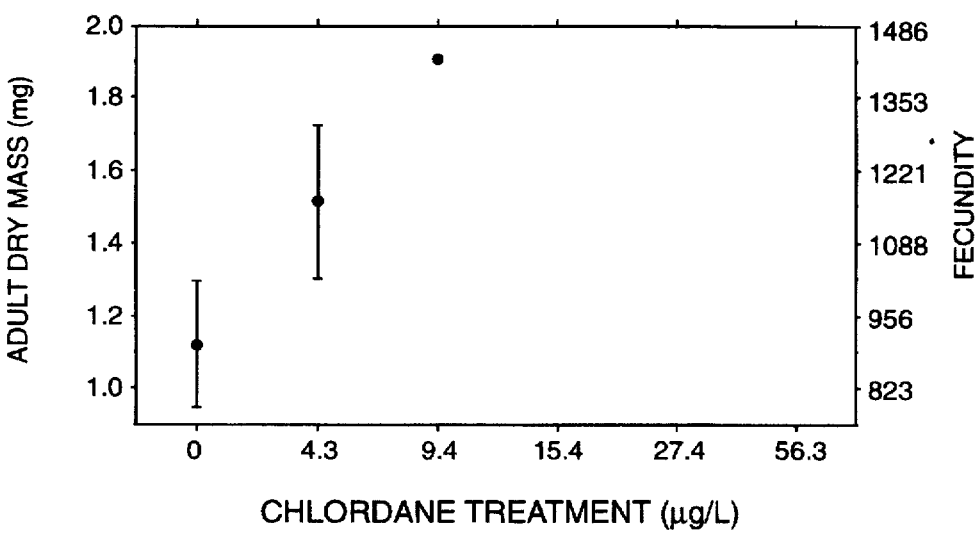

In each of FIGS. 3a, 3b and 3c, the mean is indicated by a solid dot in the 95% confidence index (C.I.) which is indicated by the vertical bar for all data relating to the control in 4.3 µg/l treatment group. Adult fecundity (Y) can be predicted from female dry mass (X) using the following equation: Y=160.7+662.4(X). Based on that relationship, as shown in FIG. 3c, mean fecundity, based on the equation, was about 890 eggs per female for the control group, about 1,155 eggs per female for the 4.3 µg/l treatment group and about 1,420 eggs per female for the 9.4 µg/l treatment group.

Egg hatch success exceeded 95% for all egg clutches obtained from adults which survived exposure as larvae to the two control and five treatment conditions (namely, 4.3, 9.4, 15.4, 27.4, and 56.3 µg/l).

Experiments lasting the duration of both the egg and the larval stages provided greater than 95% survivorship for eggs and about 80% for larvae. The larval control data compare very favorably with survivorship values ranging from 57% to 83.5% in control populations of *C. riparius* during 30 d exposure tests. Further, larval growth and development of *C. triangulifer* were readily quantifiable in assessing sublethal effects of toxic substances. Survivors in the 4.3 µg/l chlordane treatment exhibited an increase in both larval development time and size at maturity. These data are consistent, since individuals having a longer development time have a longer period to grow and, hence, achieve a larger size at maturity. That a 6% increase (2.2 d) in development time resulted in a 30% increase (0.33 mg) in size is not surprising, since larvae grow at a rate of 0.22 mg/d during the last 5 d of their larval stage at 20° C.

The experimental data indicate that the chorion of *C. triangulifer* eggs protects the embryo from external chlordane exposure up to at least 158.3 µg/l and newly hatched larvae survive without food for more than 48 h at 20° C. Further, although females accumulate a substantial body burden of chlordane (up to 140 ppb) during chronic exposure as larvae, these concentrations do not seem to interfere with the rate and success of embryonic development of their offspring. Accordingly, tests for evaluating the potential toxicity of compounds, either directly by water exposure or indirectly through bioaccumulation during feeding of the parent generation can be readily designed and implemented using *C. triangulifer*.

EXAMPLE 3

Chlordane Analysis of Test Water and Adult *C. triangulifer*

Chlordane was extracted from water samples by liquid-liquid extraction in a separatory funnel with three aliquots of hexane. PCB204 (2,2',3,4,4',5,6,6'-octachlorobiphenyl) was added as a surrogate standard before extraction. Each hexane aliquot was rinsed into the plastic sample bottle after transfer of the water sample and before its addition to the separatory funnel containing the water sample to ensure removal of chlordane adsorbed on the walls. The three hexane aliquots were combined and evaporated with a rotary evaporator and then further evaporated down to 100 µl under nitrogen for the final step. Chlordane components and metabolites were quantified from the relative responses of the surrogate standard and the authentic standards of heptachlor; trans- and cis-chlordane; trans- and cis-nonachlor; and the two metabolites, heptachlor epoxide and oxychlordane (n.b. cis-nonachlor was estimated from the response factor for trans-nonachlor). Adult body burdens and water concentrations of chlordane residue were calculated by comparison of the component areas with that of the surrogate standard to correct for losses during extraction and purification.

Adult mayflies from a given replicate vessel per treatment were dried and combined in lots of five to thirteen organisms for extraction and analysis. The mayflies were ground in 0.5 ml methanol after addition of the surrogate standard PCB204 and extracted by sonication with two 10 ml aliquots of a 1:1 methanol:methylene chloride mixture. Extracts were filtered through pasteur pipettes loaded with approximately 1.0 g of $Na_2SO_4$ and clean glass wool. Chlordane components and the surrogate standard were separated from other components in the extract on 1% deactivated silica (0.8 g) microcolumns (organochlorines were eluted with 20% methylene chloride in hexane).

Five principal chlordane components and two metabolites (heptachlor, cis- and trans-chlordane, cis- and trans-nonachlor, heptachlor epoxide, and oxychlordane) were identified and quantified by ECNI-MS, using a Hewlett Packard 5988/RTE-A mass spectrometer equipped with a Hewlett Packard 5890 GC. Instrumental conditions were: GC −0.25 mm, 30 m DB-5 column (J & W Scientific) held at 60° C. for 2 min, then ramped to 180° C. at 20°/min, to 230° C. at 2°/min, to 280° C. at 10°/min, and then held at 280° C. for 10 min; $MS-CH_4$ pressure 0.45 torr, source temperature 100° C.

Figure 4A:
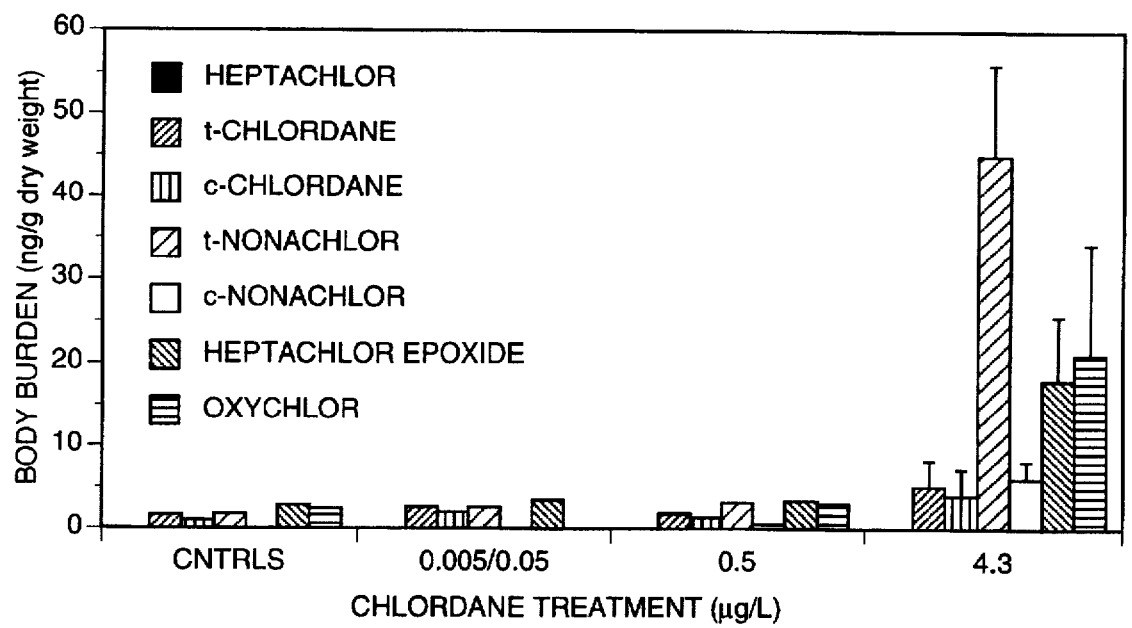
FIG. 4a shows the body burden of chlordane components and metabolites found in adult *C. triangulifer* after exposure of their larvae to different concentrations of technical chlordane.

Body burdens of chlordane compounds and metabolites were determined for adult *C. triangulifer* from three replicate rearing vessels treated with 4.3 µg/l technical chlordane. The adults contained 100±45 ppb total chlordane residue. The distribution of chlordane components and metabolites for these adults is shown in FIG. 4a, along with the distribution of compounds in adults reared at concentrations <4.3 µg/l. Adult *C. triangulifer* mayflies reared at the lower concentrations were indistinguishable from the controls with respect to pattern and concentration of components.

The relative composition of principal chlordane components or metabolites found in the *C. triangulifer* mayflies reared at 4.3 µg/l chlordane was: trans-nonachlor (45±11%), oxychlordane (21±13%), heptachlor epoxide (18±7%), cis-nonachlor (6±2%), trans-chlordane (5±3%), and cis-chlordane (4±3%). In contrast, the principal components in technical chlordane were trans-chlordane (26%), trans-nonachlor (23%), cis-chlordane (21%), heptachlor (19%), and cis-nonachlor (11%).

Figure 4B:
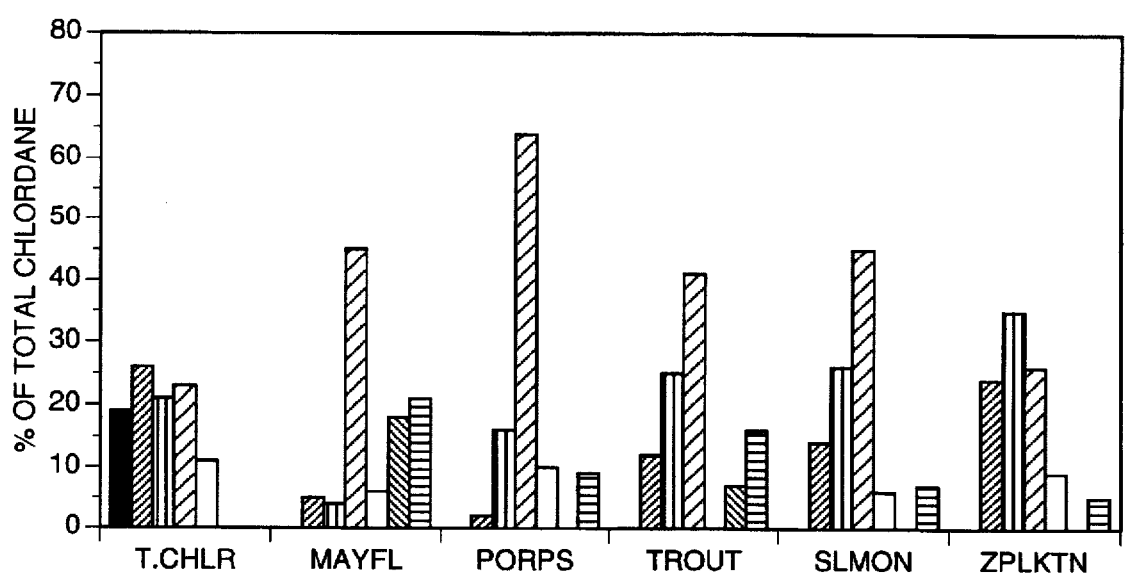
FIG. 4b shows the relative abundance of various components and/or metabolites of chlordane in *C. triangulifer* after exposure to 4.3 µg/l of technical chlordane.

FIG. 4b shows the relative amount of chlordane components in the *C. triangulifer* mayfly [MAYFL] tested as reported relating to FIG. 4a in comparison to the relative composition of chlordane components found at different times and reported by others in other animals (namely, porpoise [PORPS], salmon [SLMON], and zooplankton [ZPLKTN] found by Kawano et al., *Environ. Sci. Technol.*, 22:792-797, 1988; and lake trout [TROUT] found by Gooch et al., *Chemosphere* 21:393-406, 1990). Vertical bars for the 4.3 µg/l treatment are one standard error (Elliott, Statistical Analysis of samples of *Benthic Invertebrates*, Freshwater Biological Association Scientific Publication, Second Edition, pp. 12, 13, 80, 81, 1977).

The test results indicate that (a) heptachlor was completely metabolized by the *C. triangulifer* mayflies into heptachlor epoxide; (b) cis- and trans-chlordane were metabolized in part to oxychlordane; and (c) cis- and trans-nonachlor were poorly metabolized. The pattern of metabolism in *C. triangulifer* is strikingly similar to available data on fish and higher organisms (See FIG. 4b for data on lake trout and salmon). Because heptachlor and heptachlor epoxide were not measured in the salmon and only heptachlor epoxide was measured in the lake trout, only the chlordanes, nonachlors, and the metabolite oxychlordane could be compared. Reduced quantities of cis- and trans-chlordane relative to the nonachlors were observed in the *C. triangulifer* mayfly and salmon (but not in zooplankton), as compared to the original distribution of components in technical chlordane. In fact, the *C. triangulifer* mayflies exhibited a greater degree of transformation of the chlordanes to oxychlordane than the lake trout and salmon and an even greater level of metabolism than the zooplankton.

*C. triangulifer* seems to completely metabolize the heptachlor to heptachlor epoxide. The ratio of trans-chlordane to cis-chlordane is altered from an equal distribution in technical chlordane to a 2:1 or greater predominance of the cis- over the trans-isomer for the aquatic organisms shown for comparison purposes in FIG. 4b. *C. triangulifer* appears capable of metabolizing or excreting both isomers equally (FIG. 4b). The data support the hypothesis that the predominance of the cis- isomer may be due to the deposition and subsequent exposure of an aquatic organism to atmospherically altered chlordane residues rather than a metabolic discrimination of isomers by the analyzed organisms, since the *C. triangulifer* mayfly larvae were exposed to unaltered technical chlordane and treated both isomers equally.

It is noteworthy that trans-nonachlor, which accounts for 35 to 56% of the stored chlordane components and metabolites in *C. triangulifer*, is also the principal component found by others in several species of fish and lobster collected off the east coast of Canada, in bald eagles, and in human blood. In fact, the ratio of trans-nonachlor to cis-nonachlor in *C. triangulifer* (range 6.2-8.6) overlaps substantially with the ratio of 5:7 observed by others for marine fish and lobsters.

Data indicate that there is a clear trend for the *C. triangulifer* mayfly to bioaccumulate cis- and trans-nonachlor as well as the metabolites heptachlor epoxide and oxychlordane. Because the metabolites are several times more toxic than the original compounds, the limitation of assessing toxicity by chemical assay of the precursor pollutants is emphasized. Organisms such as *C. triangulifer* may be much more sensitive to chlordane residues than other animals due to their greater ability to metabolize the primary components of technical chlordane.

The need to employ a range of species in bioassay testing is important to the adequate evaluation and/or prediction of the impact of a chemical on a particular environment. The Examples demonstrate both the utility and the effectiveness of the mayfly *C. triangulifer* for whole life cycle bioassays. The data reveal sensitivity equal to or better than other standard bioassay species and show how various life history parameters can serve as response indices. The parthenogenetic mode of reproduction for *C. triangulifer*, combined with a relatively short embryonic and larval developmental period and overall ease of maintaining laboratory cultures provides a useful and effective bioassay system for evaluating toxicants of all kinds. Accordingly, while *C. triangulifer* has been used to detect chlordane levels using the testing procedures outlined in the preceding examples, it is to be understood that other chemicals and pollutants, as well as other substances, can be detected using any suitable bioassay or testing technique.

Although the invention has been described in considerable detail in the foregoing, it is to be understood that such detail is solely for the purpose of illustration and that variations can be made by those skilled in the art without departing from the spirit and scope of the invention except as set forth in the claims.

DEPOSIT OF BIOLOGICAL MATERIAL

Samples of the WCC 2 clone described above have been deposited under the provisions of the Budapest Treaty with the American Type Culture Collection, 12301 Parklawn Drive, Rockville, Md. 20852, on Jul. 31, 1996, under Accession No. ATCC 97673. All restrictions on the availability to the public of the deposited material will be irrevocably removed upon the granting of a patent.

We claim:

1. A method of testing for the presence of any test substance in an environment to which any life stage of at least one clone of a *Centroptilum triangulifer* mayfly is exposed and which has an effect on the mayfly comprising the steps:

(A) identifying and selecting at least one clone of *Centroptilum triangulifer* as a test clone to be subjected to the test substance;

(B) exposing each test clone to the test substance for a predetermined time; and (C) determining the effect of the test substance on each test clone by at least one of (i) observing the test clone for a lethal or sublethal effect; and (ii) sacrificing the test clone, and analyzing the sacrificed test clone for at least one of (a) the presence of at least one of the test substance and any of its metabolites, (b) the quantity of at least one of the test substance and any of its metabolites, and (c) a lethal or sublethal effect of at least one of the test substance and any of its metabolites.

2. The method of claim 1 wherein the test substance is selected from the group consisting of a stressor substance, a contaminant, a suspected contaminant and mixtures thereof.

3. The method of claim 1 wherein the sacrificed test clone is analyzed for the presence and amount of at least one of the test substance and any of its metabolites.

4. The method of claim 3 further comprising grinding and placing the sacrificed test clone into a solvent to form a solvent mixture, separating the test substance and any metabolites being tested from the solvent mixture, and identifying and quantifying the test substance and any of its metabolites.

5. The method of claim 4 wherein the test substance and any of its metabolites are identified and quantified using a mass spectrometer.

6. The method of claim 1 wherein the sacrificed test clone is analyzed using techniques selected from the group consisting of gravimetric, mass spectrometric, gas chromatographic, liquid chromatographic, atomic absorption, ion charge plasma, direct charge plasma, ultraviolet spectrophotometric techniques, and visible spectrophotometric.

7. The method of claim 1 wherein the test substance is chlordane.

8. The method of claim 1 wherein the test substance is a chlordane derivative.

9. The method of claim 8 wherein the chlordane derivative is selected from heptachlor, t-chlordane, c-chlordane, t-nonachlor, c-nonachlor, heptachlor epoxide, oxychlor and mixtures thereof.

10. The method of claim 1 wherein the sublethal effect is selected from the group consisting of size, mass, fecundity, behavior, molting, growth, respiration, feeding, digestion, assimilation, egestion, excretion, morphology, mobility, susceptibility to parasite attack, effect on developmental stages, chemosensory ability, effect on tactile sensing ability, endocrine levels, enzymatic induction and combinations thereof.

11. The method of claim 1 wherein the *Centroptilum triangulifer* test clone is a naturally existing clone of *Centroptilum triangulifer*.

12. The method of claim 11 wherein the clone is a WCC 2 clone deposited with the ATCC under Accession No. 97673.

13. The method of claim 1 wherein the test substance is a substance indicative of lethal or sublethal effects of sedimentation from point or non-point sources.

14. The method of claim 1 wherein the test substance is from any source from which the test substance may reach a fresh water environment during use, transport, or after disposal.

15. The method of claim 14 wherein the source is selected from the group consisting of effluent, runoff and spillage.

16. A method of testing for the presence of any test substance in an environment to which any life stage of at least one clone of a *Centroptilum triangulifer* mayfly is exposed and which has an effect on the mayfly comprising the steps:

(A) identifying and selecting at least one clone of *Centroptilum triangulifer* from an isolate as a test clone to be subjected to the test substance and a corresponding control clone from a different aliquot of the test clone against which the test clone will be compared;

(B) exposing each test clone, but not the corresponding control clone, to the test substance for a predetermined time; and (C) determining the effect of the test substance on each test clone by at least one of (i) observing the test clone and the corresponding control clone for a lethal or sublethal effect to determine whether the test clone has a lethal or sublethal effect in comparison to the corresponding control clone; and (ii) sacrificing the test clone and the corresponding control clone, and analyzing the sacrificed test clone and corresponding control clone for at least one of (a) the presence in the test clone compared to the corresponding control clone of at least one of the test substance and any of its metabolites, (b) the quantity in the test clone compared to the corresponding control clone of at least one of the test substance and any of its metabolites, and (c) a lethal or sublethal effect of at least one of the test substance and any of its metabolites in the test clone compared to the corresponding control clone.

* * * * *